United States Patent [19]
Stone

[11] Patent Number: 5,921,987
[45] Date of Patent: Jul. 13, 1999

[54] ARTICULAR CARTILAGE TRANSPLANT INSTRUMENT SET

[75] Inventor: Kevin R. Stone, Mill Valley, Calif.

[73] Assignee: DePuy Orthopaedic Technology, Inc., Tracy, Calif.

[21] Appl. No.: 08/797,973

[22] Filed: Feb. 12, 1997

Related U.S. Application Data

[63] Continuation-in-part of application No. 08/710,176, Sep. 13, 1996.

[51] Int. Cl.$^6$ .................................................. A61B 17/56
[52] U.S. Cl. .............................................. 606/80; 606/79
[58] Field of Search ................................. 606/79, 80, 81, 606/82, 83, 84, 85, 86, 96; 408/203.5, 204

[56] References Cited

U.S. PATENT DOCUMENTS

| | | | |
|---|---|---|---|
| 4,573,838 | 3/1986 | Omi et al. | 408/204 |
| 5,556,399 | 9/1996 | Huebner | 606/80 |
| 5,632,747 | 5/1997 | Scarborough et al. | 606/79 |

Primary Examiner—Guy V. Tucker
Attorney, Agent, or Firm—Lappin & Kusmer LLP

[57] ABSTRACT

The invention disclosed is a method and instrument set for repairing focal arthritic defects in a mammalian joint, especially in a human knee. The articular cartilage transplantation instrument set includes a coring device and first and second obturators. The coring device includes a cylindrical tube extending a distance along a coring axis between distal and proximal ends. A set of cutting elements or teeth are disposed at the distal end, and a gripper is at the proximal end. The outer diameters of the obturators are slightly less than the inner diameter of the tube of the coring device so that each of the obturators may be slidingly within the tube of the device with each of the respective obturator axes being substantially coaxial with the axis of the of the coring device tube. The length of the first obturator is selected so that when its rod is positioned all the way into the tube of the device, the distal end of the obturator is displaced by a distance X1 from the distal end of the device. The length of the second obturator is selected so that when the second obturator is fully positioned within the device 12, the end of the second obturator is substantially at (or extends beyond) the distal end of the device 12.

4 Claims, 5 Drawing Sheets

ND INSTRUMENT SET

ARTICULAR CARTILAGE TRANSPLANT INSTRUMENT SET

REFERENCE TO RELATED APPLICATION

This application is a continuation-in-part of U.S. Pat. application Ser. No. 08/710,176, filed Sep. 13, 1996 still pending.

The present invention relates to the field of surgical methods and instruments for treatment of a focal arthritic defect in a joint of a mammal, and more particularly, for treatment of focal arthritic defects in the knee of a mammal.

BACKGROUND OF THE INVENTION

Focal arthritic defects are defined as areas of complete hyaline cartilage loss exposing the underlying bone ringed by areas of intact hyaline cartilage. Focal arthritic defects may occur as the result of trauma or other conditions, such as loss of the protective meniscus cartilage or osteoarthritis. Focal arthritic defects may occur in any joint, being especially problematic in the weight-bearing joints, i.e., in the hip, the knee, and the ankle. Focal arthritic defects in these joints lead to pain, swelling, and loss of motion. In the past, treatment of focal arthritic defects has included drilling, abrasion, periosteal covering and bone grafting.

SUMMARY OF THE INVENTION

The present invention provides a surgical technique in which an osteocartilaginous plug, or graft, can be removed from one location within a mammalian joint and moved to another location within the joint, or to another joint, to fill a focal arthritic defect. In one embodiment, the invention provides a method of repairing an arthritic defect in a mammalian joint which comprises the steps of forming a roughened, bleeding surface of cancellous bone within the defect; forming a plug of osteocartilaginous tissue from an undamaged site within the joint or from another joint; removing said plug from said undamaged site; and inserting the plug into the defect, positioning said plug against the roughened bleeding surface, and holding the plug in place for a time sufficient to allow a blood clot to form between said plug and said roughened bleeding surface.

The invention includes an instrument set that may be used to effect the above described surgical technique. The instrument set preferably includes a coring device and two obturators. The first obturator is used with the coring device to harvest articular cartilage and cancellous bone from a site within the intercondylar notch, and the second obturator is used with the coring device to transplant the harvested articular cartilage and cancellous bone.

BRIEF DESCRIPTION OF THE DRAWINGS

For a fuller understanding of the nature and the objects of the invention, reference should be made to the following detailed description and the accompanying drawings in which like reference numerals refer to like elements and in which.

DESCRIPTION OF THE PREFERRED EMBODIMENT

Figure 1:
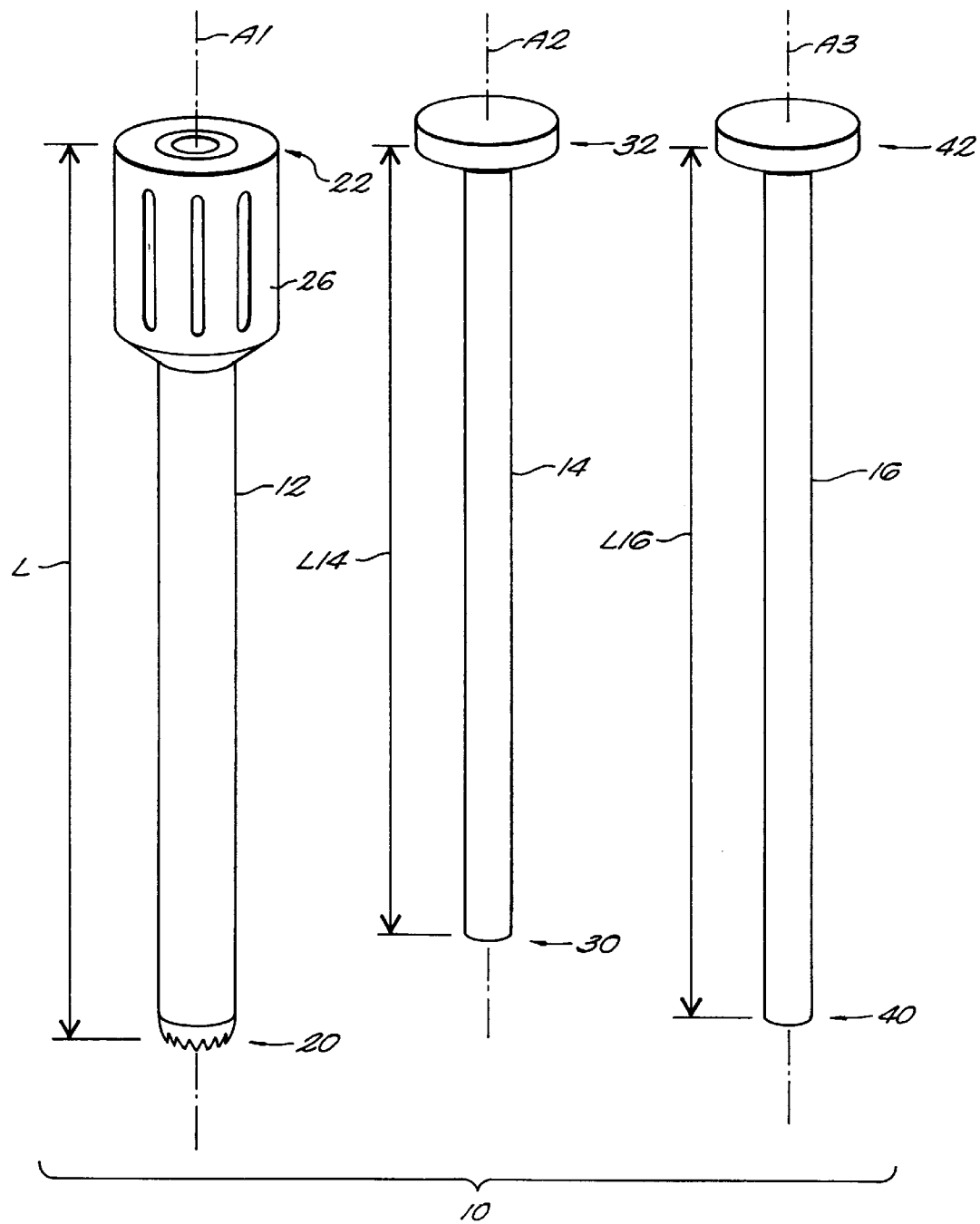
FIG. 1 shows, in perspective view, an instrument set embodying the invention.

The method of the invention is suitable for repairing any arthritic defect in any joint, so long as the defect is not so extensive that no undamaged portion of the joint remains. Preferably, the method of the invention is used to repair focal arthritic defects in the hip. More preferably, the method of the invention is used to repair focal arthritic defects in the ankle. Most preferably, the method of the invention is used to repair focal arthritic defects in the knee. Focal arthritic defects in the joints of any mammal may be repaired in accordance with the method of the invention. Preferably, focal arthritic defects in the joints of humans may be repaired using the method of the invention.

For example, when the joint being repaired is a knee, after routine arthroscopic examination has been performed and a focal arthritic defect has been identified, the procedure is performed as follows.

The base of the arthritic defect where the exposed bone is visualized, is prepared by fracturing with arthroscopic awls similar to ice picks. Preferably, the fracture holes are approximately 5–10 mm deep, with an inter-hole spacing in the range 1–5 mm, and most preferably 2–3 mm. Fracturing of the base produces bleeding. The blood forms clots over the roughened cancellous bone exposed by the fracturing. Attention is next turned to the intercondylar notch between the two femoral condyles. Within the notch lies the anterior and posterior cruciate ligaments. The area anterior to the anterior cruciate ligament on the medial wall of the lateral femoral condyle is exposed with a curette, removing overlying soft tissue. A metal trephine coring device is then manually bored into the osteocartilaginous surface and down into the underlying cancellous bone to establish an osteocartilaginous graft. Preferably, the graft has a thickness in the range 1–2 cm. The bore is then backed out into the knee joint and then pointed at the prepared bed of the arthritic defect. The core of osteocartilaginous tissue, i.e., the graft, is then pushed into the defect with the plunger and held in place for three minutes. As blood clots, the graft is secured by the adhesive properties of the clot. The instruments are then removed and the patient kept non weight-bearing for four weeks.

In one form of the invention, prior to insertion, the osteocartilaginous graft may be exposed to a proteinaceous factor which stimulates the formation of cartilage. Any cartilage-stimulating factor may be used in this embodiment, so long as the factor is capable of increasing the amount or rate of formation of cartilaginous tissue within a joint. For example, the graft may be exposed to a cartilage-stimulating factor belonging to the transforming growth factor-β (TGF-β) supergene family. Such a cartilage-stimulating factor may be in homodimeric or heterodimeric form. The cartilage-stimulating factor may be purified from mammalian tissue or it may produced recombinantly from one or more cDNAs encoding a monomer of the cartilage-stimulating factor. The graft is exposed to a therapeutically effective amount of the cartilage-stimulating factor. As used herein, a "therapeutically effective amount" means the total amount of cartilage-stimulating factor sufficient to show a meaningful patient benefit, ie., to enhance formation of cartilage in the vicinity of the graft.

Figure 2:
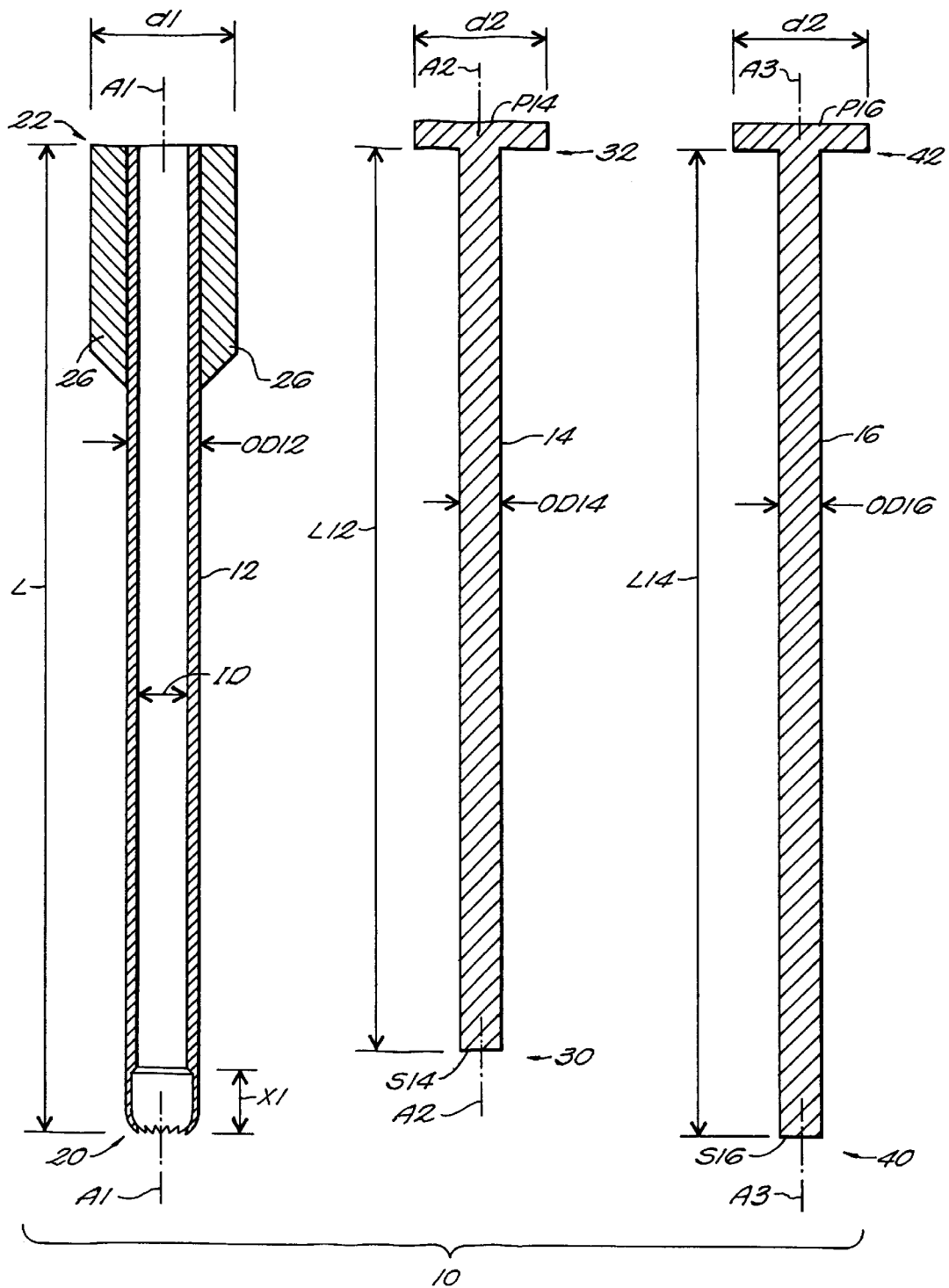
FIG. 2 shows, in sections, the instrument set of FIG. 1.

The method of the invention is preferably implemented using the articular cartilage instrument set 10 illustrated in FIGS. 1 and 2. The set 10 includes a coring device 12 and a first obturator 14 and a second obturator 16. The coring device 12 includes a cylindrical tube extending a distance along a coring axis A1 between a distal end 20 and a proximal end 22. A set of cutting elements 23, or teeth, are disposed at the distal end 20, and a gripper receiving is at the proximal end. A gripper 26 extends transverse to the axis A1 near the proximal end. In the illustrated embodiment, the gripper is in the form of a cylindrical shell extending about the proximal end to tube 12 (but other forms may be used ) which permits a surgeon to grip the coring device 12 with his or her hand and reciprocally rotate that element about axis A1 and apply an axial force in the direction of axis A1.

The obturators 14 and 16 each include cylindrical rods extending along a respective one of obturator axes A2 and A3 between distal ends 30, 40 and proximal ends 32, 42 respectively. Each of the rods has a surface S14, S16 at its distal end which extends at least partially transverse to the respective axes A2 and A3. In the illustrated embodiment, the surfaces S14, S16 are planar and perpendicular to axes A2, A3, but in other embodiments, different shapes may be used, e.g. convex, concave or irregular. The outer diameters OD14, OD16 of the rods are slightly less than the inner diameter ID of the tube of coring device 12 so that the obturator may be slidingly within the tube of device 12 with axes A2 and A3 being substantially coaxial with axis A1. Pusher sections P14, P16 are positioned at the proximal ends of the rods of obturators 14 and 16, respectively. The pusher sections P14, P16 have outer diameters d2 larger then ID of device 12. The pusher sections P14, P16 may have rounded ends to permit a surgeon to easily apply an axial force by hand, while gripping the gripper member 26.

The length L14 of obturator 14 is selected so that when its rod is positioned all the way into the tube of device 10, i.e. with section P14 adjacent to end 22 of tube 12, the distal end 30 of obturator 14 is displaced by distance X1 from the end 20 of device 12. The length L16 of obturator 16 is selected so that when obturator 16 is fully positioned within device 12, i.e. with section P16 adjacent to end 22 of tube 12, the end 40 of obturator 16 is substantially at (or extends beyond) the distal end 20 of device 12. Variations of the lengths L14 and L16 are within the scope of the invention. Other dimensions of the instruments are indicated by reference designators in FIG. 2. In the preferred embodiment:

L=20 cm
OD12=6 (or 11) mm
d1=20 mm
d2=20 mm
ID=4 (or 9) mm
ID2=5 (or 10) mm
X1=2 cm
L14=18 cm
L16=20 cm

FIGS. 3–7 illustrate the method of the invention, using a variant of the instrument set of FIGS. 1 and 2. In that embodiment, the tube of coring device 10 has a constant outer diameter along its length. In one form, the inner surface of the tube 12 is "rifled", i.e. has one or more helical grooves (HG) extending about the coring axis A1, near the distal end of device 12, to aid in keeping the harvested cartilage and cancellous bone in place. In another form, as illustrated in FIGS. 1 and 2, that inner surface defines a larger diameter (ID2) region near the distal end 20 than at other locations along its length.

Figure 3:
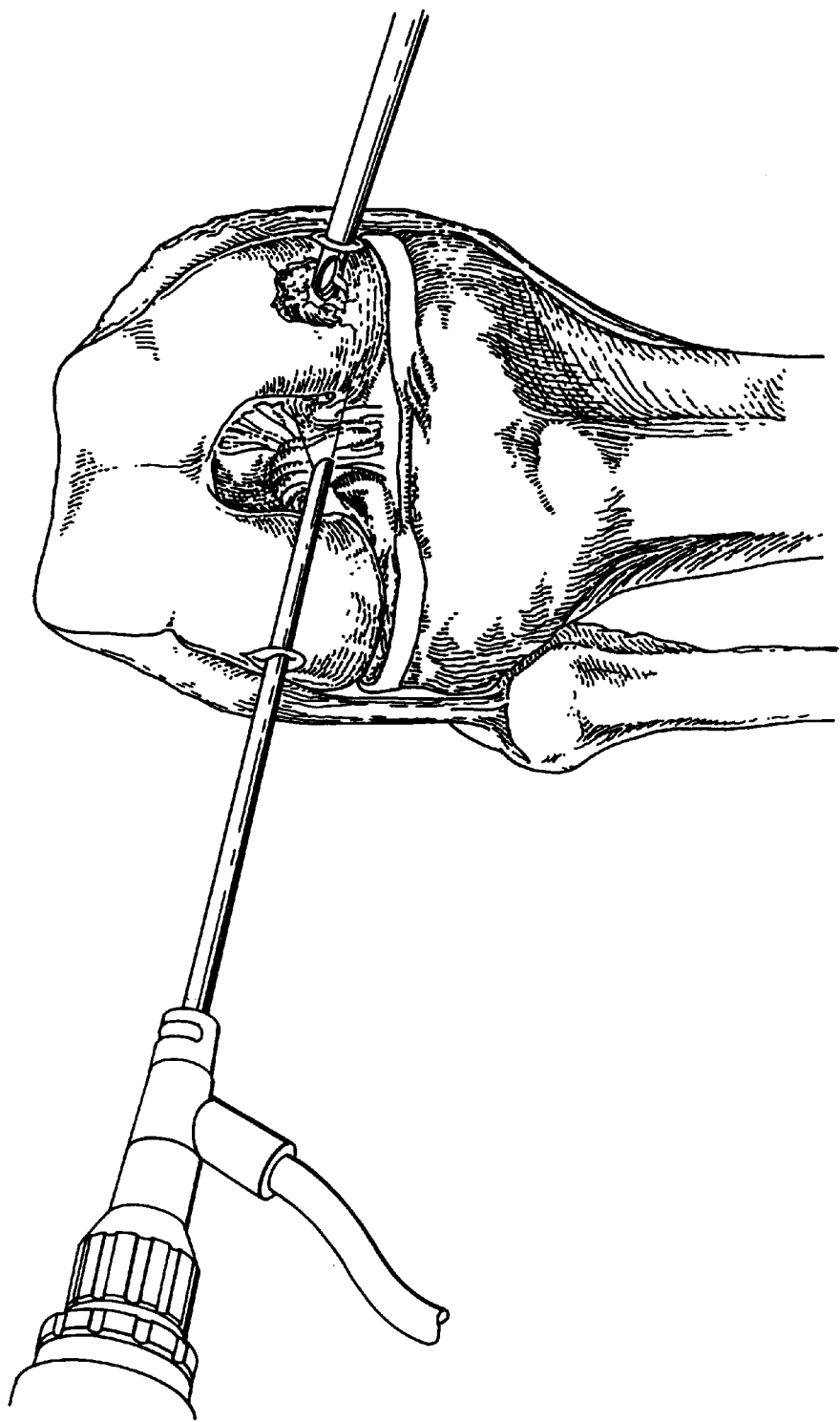
FIG. 3 illustrates shaving of articular cartilage according to a method of use of an instrument set embodying the invention.
Figure 4:
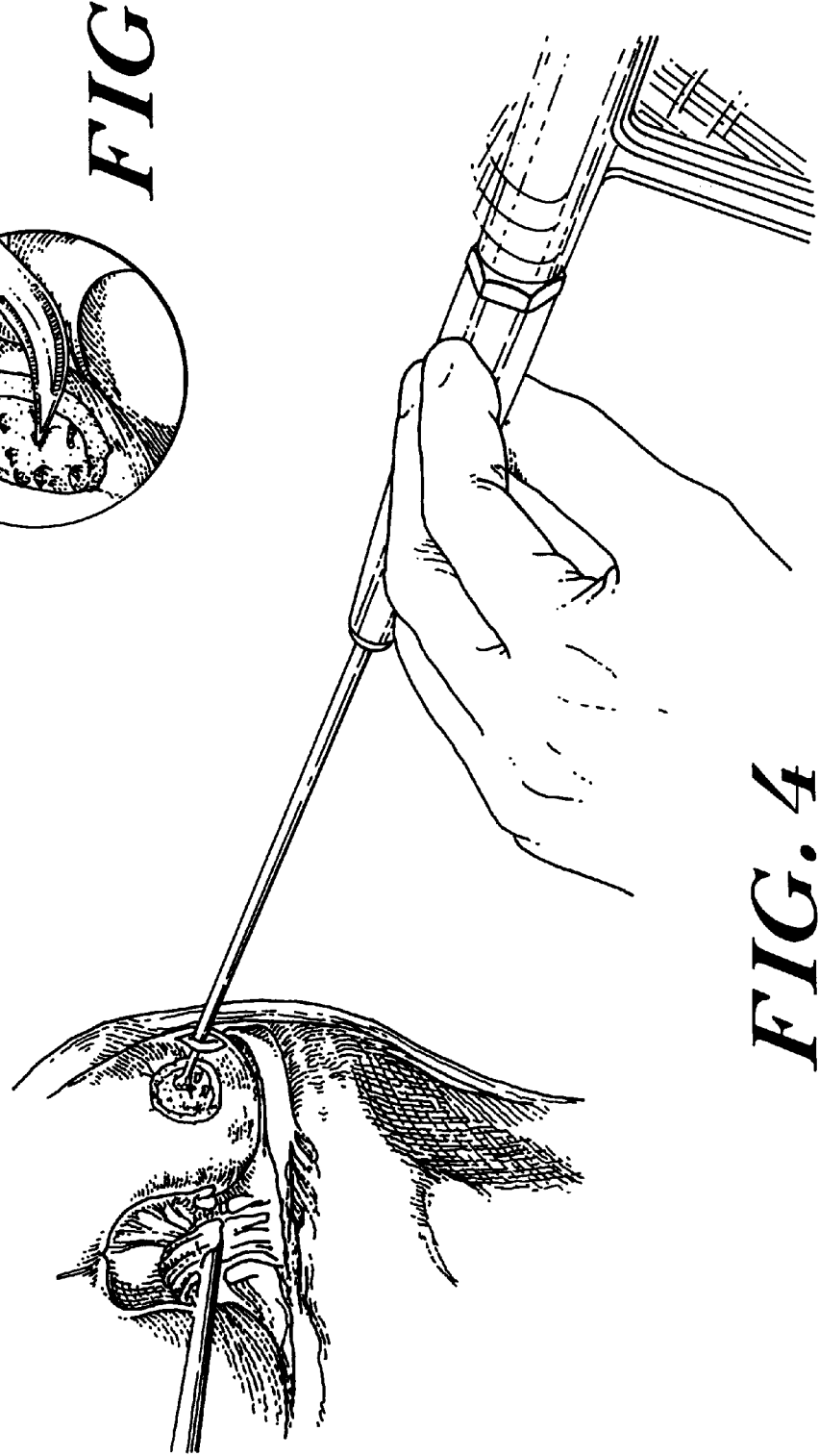
FIG. 4 shows microfracture preparation of the base of a chondral lesion prior to articular cartilage grafting according to a method of use of an instrument set embodying the invention.
Figure 4A:
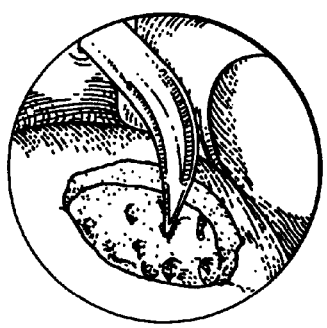
Figure 5:
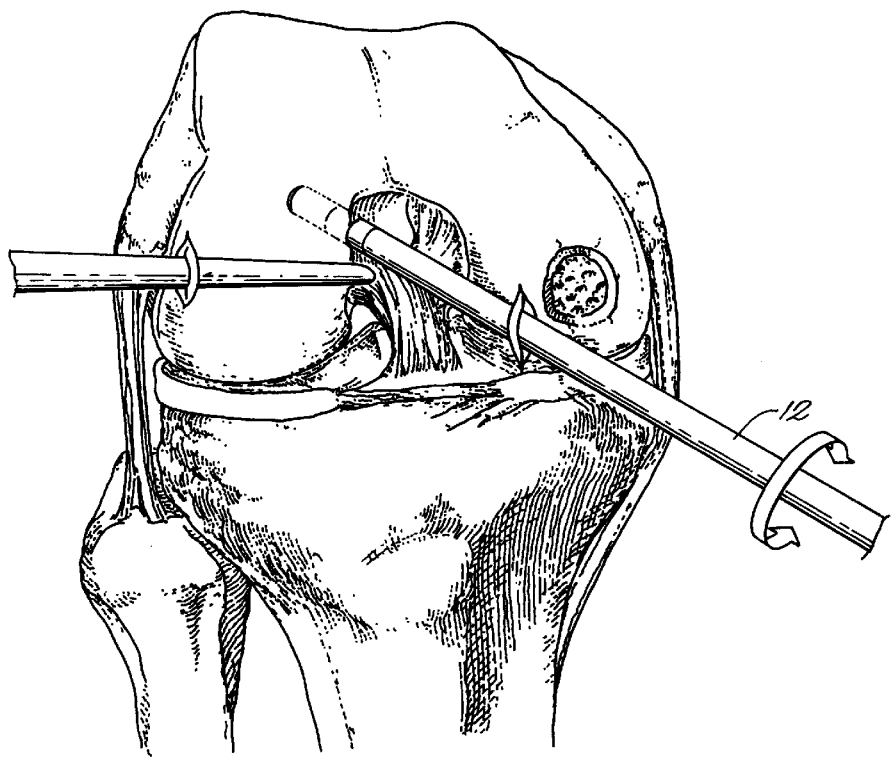
FIG. 5 shows harvesting of articular cartilage with cancellous bone from the intercondylar notch according to a method of use of an instrument set embodying the invention.
Figure 6:
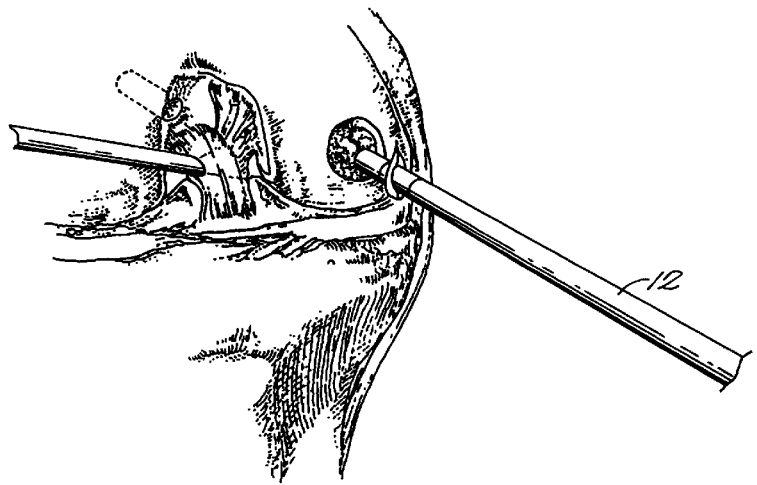
FIG. 6 shows transplantation of the articular cartilage and cancellous bone graft to the prepared chondral defect according to a method of use of an instrument set embodying the invention.
Figure 7:
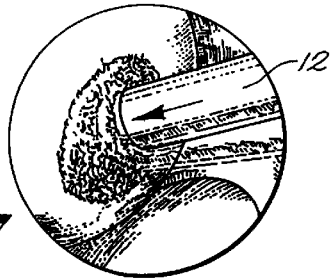
FIG. 7 shows transplantation of the articular cartilage and cancellous bone graft to the prepared chondral defect according to a method of use of an instrument set embodying the invention.

In FIG. 3, the first step of articular cartilage transplantation is shown, demonstrating shaving of articular cartilage lesion. FIG. 4 shows microfracture preparation of the base of a chondral lesion prior to articular cartilage grafting. FIG. 5 shows harvesting of articular cartilage with cancellous bone from the intercondylar notch. FIGS. 6 and 7 show transplantation of the articular cartilage and cancellous bone graft to the prepared chondral defect. In some forms of the invention, the harvested articular cartilage and cancellous bone is crushed and mixed before transplantation.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. An articular cartilage transplantation instrument set consisting of:

A. a coring device including an elongated cylindrical tube extending a distance along a coring axis between a distal and proximal end, said tube having a set of cutting elements at said distal end, and including a gripper extending transverse to said coring axis near said proximal end, wherein said tube has an inner surface characterized by an inner diameter ID at least extending from said proximal end, B. a first obturator including an elongated cylindrical rod having an outer diameter slightly less than ID and extending a distance L14 along a first obturator axis between a distal end and a proximal end, said proximal end including an end surface at least in part transverse to said first obturator axis, and including at said proximal end a pusher section having a transverse dimension greater than ID, said first obturator being adapted so that its proximal end may be slidingly positioned within said cylindrical tube with said pusher section interferingly engaging with said proximal end so that said distal end of said first obturator is within said tube and axially displaced by X1 from said distal end of said tube, and C. a second obturator including, an elongated cylindrical rod having an outer diameter slightly less than ID and extending a distance L16 along a second obturator axis between a distal end and a proximal end, said proximal end including an end surface at least in part transverse to said second obturator axis, and including at said proximal end a pusher section having a transverse dimension greater than ID, said second obturator being adapted so that its proximal end may be slidingly positioned within said cylindrical tube with said pusher section interferingly engaging with said proximal so that said distal end of said second obturator is within said tube and is at or extends beyond said distal end of said tube.

2. The instrument set according to claim 1 wherein said inner surface near said distal end is irregular.

3. The instrument set according to claim 1 wherein said inner surface includes at least one helical groove extending about said coring axis.

4. The instrument set according to claim 1 wherein said inner surface is cylindrical within X1 of said distal end of said tube, where said inner surface of said tube defines a cylindrical region within X1 of said distal end, wherein said cylindrical region has a diameter greater than ID.

* * * * *